US 8,198,090 B2
Jun. 12, 2012

(12) United States Patent
Kubo et al.

(10) Patent No.: US 8,198,090 B2
(45) Date of Patent: Jun. 12, 2012

(54) CARTRIDGE, RESIDUAL LIQUID REMOVING METHOD, AND AUTOMATIC ANALYZER

(75) Inventors: Kosuke Kubo, Kyoto (JP); Junichi Oka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 12/444,828

(22) PCT Filed: Oct. 4, 2007

(86) PCT No.: PCT/JP2007/069469
§ 371 (c)(1),
(2), (4) Date: Apr. 8, 2009

(87) PCT Pub. No.: WO2008/044594
PCT Pub. Date: Apr. 17, 2008

(65) Prior Publication Data
US 2010/0075426 A1    Mar. 25, 2010

(30) Foreign Application Priority Data
Oct. 10, 2006   (JP) ................................. 2006-276971

(51) Int. Cl.
*G01N 35/02* (2006.01)
*G01N 1/00* (2006.01)
*B08B 5/04* (2006.01)
*B08B 9/00* (2006.01)

(52) U.S. Cl. ................ 436/49; 436/47; 436/43; 422/90; 422/50

(58) Field of Classification Search .................... 436/49, 436/47, 43; 422/100, 103, 99, 50
See application file for complete search history.

(56) References Cited

U.S. PATENT DOCUMENTS

| 3,999,505 | A | 12/1976 | Kato et al. |
|---|---|---|---|
| 4,070,986 | A | 1/1978 | Kato et al. |
| 4,827,780 | A | 5/1989 | Sarrine et al. |
| 4,847,050 | A * | 7/1989 | Jenkins et al. ............... 422/102 |
| 6,027,695 | A * | 2/2000 | Oldenburg et al. ............ 506/39 |
| 2005/0092685 | A1* | 5/2005 | Hilhorst et al. ............... 210/656 |
| 2006/0120926 | A1 | 6/2006 | Takada et al. |

FOREIGN PATENT DOCUMENTS

| JP | 51-035393 | 3/1976 |
|---|---|---|
| JP | 51-037691 | 3/1976 |
| JP | 58-036359 | 3/1983 |
| JP | 58-048647 | 4/1983 |
| JP | 58-193255 | 12/1983 |
| JP | 60-243566 | 12/1985 |

(Continued)

*Primary Examiner* — Christine T Mui
(74) *Attorney, Agent, or Firm* — Morgan, Lewis & Bockius LLP (57) ABSTRACT

A cartridge is provided that can remove a residual liquid all around the leading end of a pipette, without requiring any new equipment, regardless of the viscosity of the residual liquid. This cartridge includes a plurality of tanks, each of which has an upper opening, and a liquid is introduced into or led out from at least one of the plurality of tanks 110 to 119 with a pipette. The cartridge further includes waste liquid tanks 120 to 122. The waste liquid tanks 120 to 122 each includes a capillary phenomenon generation portion. A residual liquid present at the leading end of the pipette is brought into contact with the capillary phenomenon generation portion of the waste liquid tanks, and the residual liquid is transferred to the capillary phenomenon generation portion through the capillary phenomenon to be removed from the pipette.

11 Claims, 5 Drawing Sheets

FOREIGN PATENT DOCUMENTS

| | | |
|---|---|---|
| JP | 7-003329 | 1/1995 |
| JP | 8-122336 | 5/1996 |
| JP | 2669821 | 7/1997 |
| JP | 11-316226 | 11/1999 |
| JP | 2004-203390 | 7/2004 |
| JP | 2007-175005 | 7/2007 |

* cited by examiner

CARTRIDGE, RESIDUAL LIQUID REMOVING METHOD, AND AUTOMATIC ANALYZER

TECHNICAL FIELD

The present invention relates to cartridges, residual liquid removing methods, and automatic analyzers.

BACKGROUND ART

Conventionally, an automatic analyzer is used that automatically measures the amount of a predetermined component in a sample by detecting the reaction between the sample and a reagent in, for example, biochemical tests or laboratory tests. In this measurement with the automatic analyzer, cartridges are used that have reagent tanks filled with reagents as well as reaction tanks in which a sample and a reagent are reacted with each other (see, for instance, Patent Documents 1 to 3).

Figure 8:
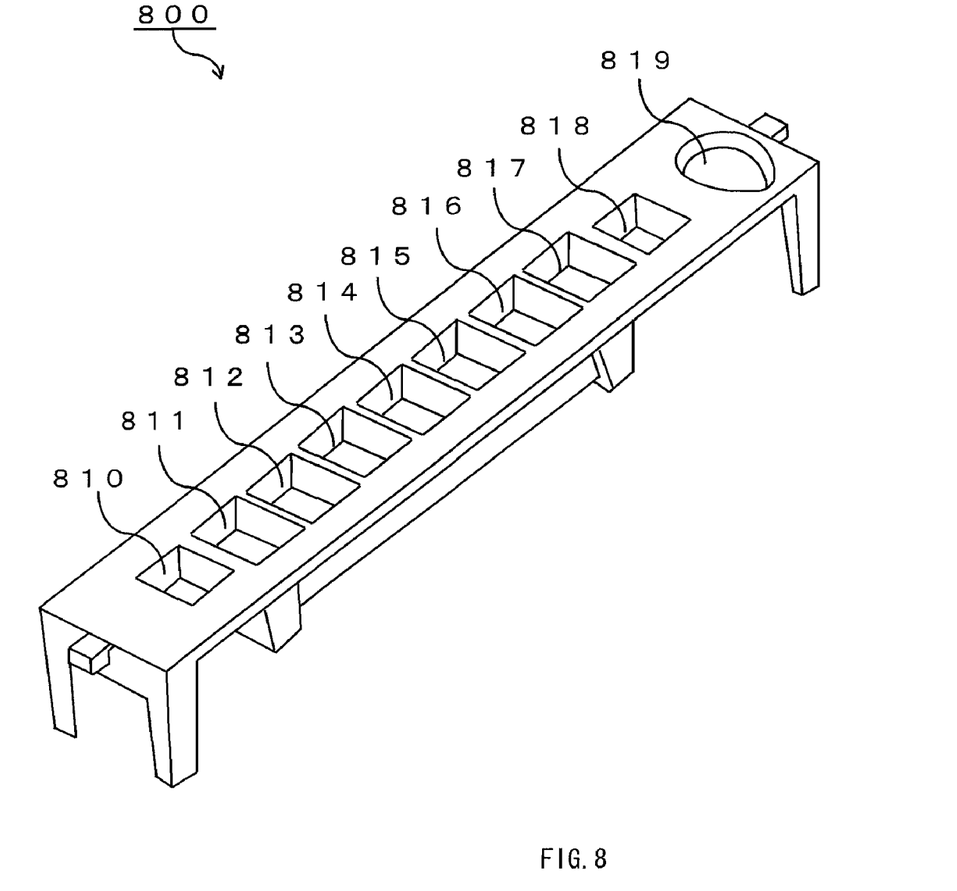
FIG. 8 is a perspective view showing the configuration of an example of a conventional cartridge.

FIG. 8 shows an example of a conventional cartridge. As shown in FIG. 8, the cartridge 800 includes a plurality of (10 in this example) tanks 810 to 819 that are disposed in parallel with each other in the longitudinal direction and are unified with a plate member. The upper parts of the plurality of tanks 810 to 819 are open. Once this cartridge 800 is set on an automatic analyzer, a sample or a reagent that has been stored in each of the plurality of tanks 810 to 819 is introduced or led out with a vertically and horizontally movable pipette provided for the automatic analyzer.

In the measurement that is carried out using such a cartridge, when, for example, a sample or a reagent remains at the leading end of the pipette, the measurement reliability is deteriorated. In the case where the residual liquid present in/on the pipette is not removed, it is necessary to replace the chip mounted on the leading end of the pipette every time a liquid is drawn therein or discharged therefrom. Accordingly, it is necessary to remove the residual liquid present at the leading end of the pipette. The method of removing the residual liquid is, for example, a method that includes providing a waste liquid tank for the cartridge and bringing a side face of the pipette into contact with a side wall of the waste liquid tank. In this method, however, it is difficult to remove the liquid that has adhered to the opposite side face of the pipette to the side that is brought into contact with a side wall of the waste liquid tank.

Furthermore, there are methods for removing the residual liquid by completely discharging the air in the pipette or by blowing air onto the leading end of the pipette. In these methods, however, an air feeder must be provided and any highly viscous liquid tends to remain in the pipette.

Furthermore, various methods have been proposed in which the leading end of the pipette is brought into contact with filter paper and thereby the residual liquid is absorbed thereby (see, for example, Patent Documents 4 to 10). However, this method requires equipment for recovering the used filter paper (after absorption) and providing a new filter paper.
[Patent Document 1] JP 58-36359 U
[Patent Document 2] JP 8-122336 A
[Patent Document 3] JP 11-316226 A
[Patent Document 4] JP 51-35393 A
[Patent Document 5] JP 51-37691 A
[Patent Document 6] JP 58-48647 U
[Patent Document 7] JP 58-193255 U
[Patent Document 8] JP 60-243566 A
[Patent Document 9] JP 7-3329 U
[Patent Document 10] JP 2669821 B

DISCLOSURE OF INVENTION

Accordingly, the present invention is intended to provide a cartridge that can remove a residual liquid all around the leading end of a pipette, without requiring any new equipment, regardless of the viscosity of the residual liquid.

In order to achieve the aforementioned object, the cartridge of the present invention has a plurality of tanks, each of which has an upper opening, and a liquid is introduced into or led out from at least one of the plurality of tanks with a pipette. The cartridge further includes a waste liquid tank that has a capillary phenomenon generation portion. A residual liquid present at the leading end of the pipette is brought into contact with the capillary phenomenon generation portion of the waste liquid tank and thereby the residual liquid is transferred to the capillary phenomenon generation portion through the capillary phenomenon to be removed from the pipette.

A residual liquid removing method of the present invention is a residual liquid removing method for removing a residual liquid present in/on a pipette of an automatic analyzer, wherein the method includes:

preparing a cartridge comprising a plurality of tanks, each of which has an upper opening, and a waste liquid tank, with the waste liquid tank having a capillary phenomenon generation portion, mounting the cartridge on the automatic analyzer equipped with the pipette that is movable vertically and horizontally, introducing a liquid into or leading out the liquid from at least one of the plurality of tanks with the pipette, and bringing the residual liquid present at the leading end of the pipette into contact with the capillary phenomenon generation portion of the waste liquid tank and thereby transferring the residual liquid to the capillary phenomenon generation portion through the capillary phenomenon to remove the residual liquid from the pipette.

An automatic analyzer of the present invention is an automatic analyzer, on which a cartridge is mounted detachably, including a vertically and horizontally movable pipette, wherein the cartridge includes a plurality of tanks, each of which has an upper opening, and a waste liquid tank, the waste liquid tank has a capillary phenomenon generation portion, a liquid is introduced into or led out from at least one of the plurality of tanks with the pipette, and a residual liquid present at the leading end of the pipette is brought into contact with the capillary phenomenon generation portion of the waste liquid tank and thereby the residual liquid is transferred to the capillary phenomenon generation portion through the capillary phenomenon to be removed from the pipette.

As described above, the cartridge of the present invention has a capillary phenomenon generation portion provided for a waste liquid tank, and the capillary phenomenon thereof is utilized to transfer a residual liquid present at the leading end of a pipette into the capillary phenomenon generation portion to remove the residual liquid. Accordingly, the cartridge of the present invention can remove the residual liquid without requiring, for example, an air feeder or a filter paper recovery unit as in the conventional cases. Furthermore, the cartridge of the present invention can remove the residual liquid all around the leading end of the pipette regardless of the viscosity of the residual liquid. Moreover, when the cartridge of the present invention is employed, it can be used repeatedly without replacing a pipette chip.

BEST MODE FOR CARRYING OUT THE INVENTION

In the present invention, the term "pipette" embraces, for example, not only a so-called pipette such as a graduated tube but also one with a chip mounted on the leading end of a pipette, a nozzle provided, for example, for an automatic analyzer, and one with a chip mounted on the leading end of the nozzle.

In the cartridge, the residual liquid removing method, and the automatic analyzer of the present invention, the capillary phenomenon generation portion is preferably a space that is formed in at least one of the bottom and side walls of the waste liquid tank and allows a capillary phenomenon to be generated.

In the cartridge, the residual liquid removing method, and the automatic analyzer of the present invention, it is preferable that a groove be formed in at least one of the bottom and side walls of the waste liquid tank, and the groove be the space that allows a capillary phenomenon to be generated. In this case, the groove has a width in the range of, for example, 0.1 to 1 mm and a depth in the range of, for example, 0.3 to 1 mm.

In the cartridge, the residual liquid removing method, and the automatic analyzer of the present invention, the capillary phenomenon generation portion may be a porous body disposed in the waste liquid tank. In this manner, when a porous body, a portion for removing a residual liquid present at the leading end of a pipette, is unified with the cartridge, the cartridge allows a residual liquid present at the leading end of a pipette to be removed without requiring any new equipment.

In the cartridge, the residual liquid removing method, and the automatic analyzer of the present invention, the number of the waste liquid tanks is not particularly limited and can be determined suitably, for example, with consideration given to the number of the types of, for example, reagents or samples to be stored in the cartridge. The number is, for example, in the range of 1 to 10, preferably in the range of 2 to 6, and more preferably in the range of 3 to 4. When the cartridge of the present invention includes a plurality of the waste liquid tanks, different types of residual liquids can be transferred to each capillary phenomenon generation portion of separate waste liquid tanks. As a result, different types of residual liquids can be prevented from being contaminated with each other, which is more preferable.

In the cartridge, the residual liquid removing method, and the automatic analyzer of the present invention, when the residual liquid is transferred to the capillary phenomenon generation portion, the distance between the leading end of the pipette and the capillary phenomenon generation portion is, for example, in the range of 0.0 to 0.7 mm.

In the cartridge, the residual liquid removing method, and the automatic analyzer of the present invention, it is preferable that the plurality of tanks include a storage tank for storing a reagent as well as a reaction tank where the reagent and a sample are reacted with each other. In this case, preferably, the plurality of tanks further include a preparation tank for preparing the sample.

In the cartridge, the residual liquid removing method, and the automatic analyzer of the present invention, at least one of the plurality of tanks may be used as a measurement cell for measuring absorbance.

In the cartridge, the residual liquid removing method, and the automatic analyzer of the present invention, the whole cartridge has a length, for example, in the range of 1 to 10 cm, a width, for example, in the range of 0.3 to 3 cm, and a height, for example, in the range of 0.5 to 5 cm.

In the cartridge, the residual liquid removing method, and the automatic analyzer of the present invention, in order to prevent a foreign substance from being mixed, it is preferable that before use, a part or all of the upper openings of the plurality of tanks be sealed with a sealing material. In this case, preferably, the sealing material is aluminum foil.

The cartridge of the present invention is not limited in the method of its use and is used in, for example, an automatic analyzer for analyzing a sample.

Next, the cartridge, the residual liquid removing method, and the automatic analyzer of the present invention are described.

Figure 1:
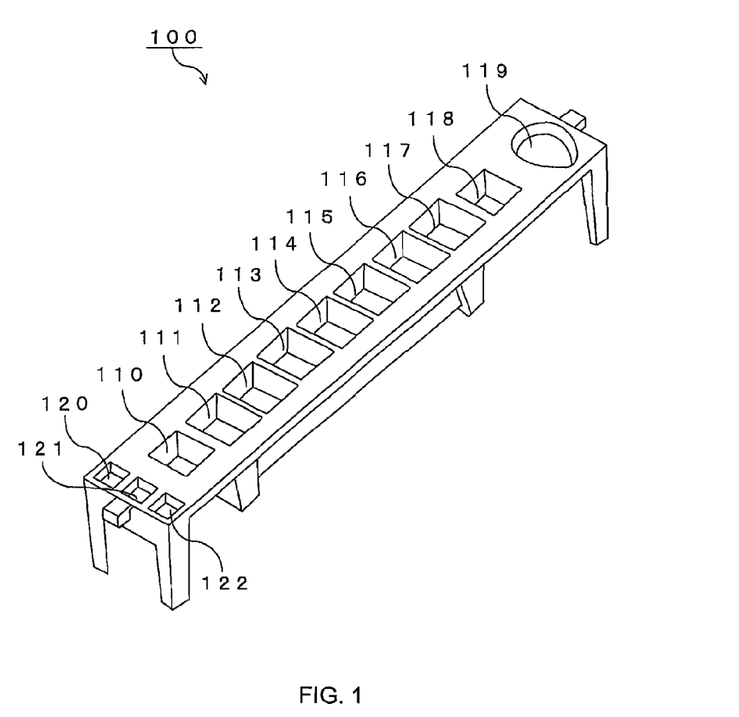
FIG. 1 is a perspective view showing the configuration of an example of the cartridge according to the present invention.
Figure 2:
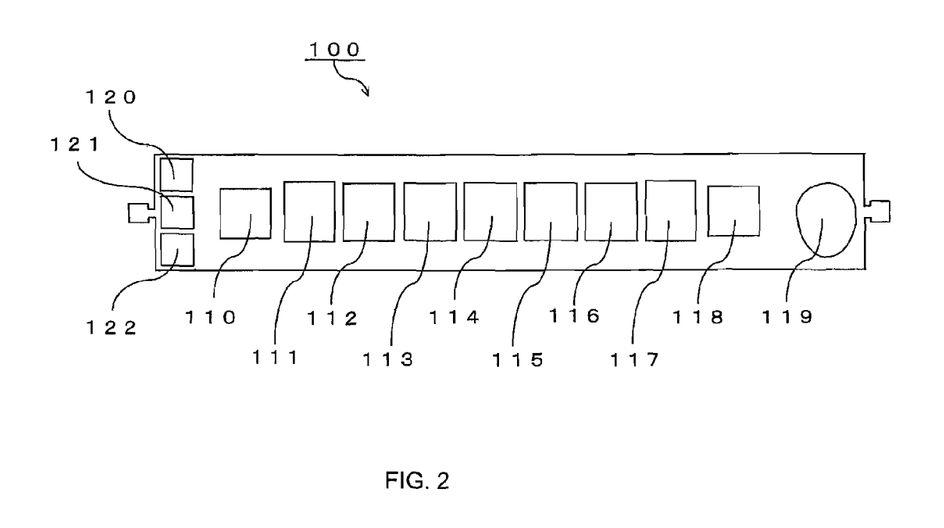
FIG. 2 is a plan view of the cartridge shown in FIG. 1.

FIGS. 1 and 2 show the configuration of an example of the cartridge of the present invention. FIG. 1 is a perspective view of the configuration of an example of the cartridge of the present invention. FIG. 2 is a plan view of the cartridge shown in FIG. 1.

As shown in FIGS. 1 and 2, this cartridge 100 includes a plurality of (10 in this case) tanks 110 to 119 and three waste liquid tanks 120 to 122. The plurality of tanks 110 to 119 are arranged in parallel with each other in the longitudinal direction of the cartridge 100 and are unified with a plate member. The upper parts of the plurality of tanks 110 to 119 are open. The three waste liquid tanks 120 to 122 are arranged at one end (the left end in FIGS. 1 and 2) of the cartridge 100 in parallel with each other in the width direction of the cartridge 100.

Preferably, the whole cartridge 100 is transparent. When the whole cartridge is transparent, the absorbance measurement described later can be carried out easily. The cartridge can be transparent, for example, only in the portion thereof through which light is transmitted when the absorbance measurement described later is performed. For example, when at least one of the plurality of tanks is transparent, the transparent tank can be used as a measurement cell for measuring absorbance.

The size of the cartridge 100 is not particularly limited. For example, it has a length of 1 to 10 cm, a width of 0.3 to 3 cm, and a height of 0.5 to 5 cm.

The material for forming the cartridge 100 is not particularly limited. Examples thereof include polystyrene resin, polyethylene resin, and polypropylene resin.

The size and shape of each tank of the plurality of tanks 110 to 119 are not particularly limited. The shape of each tank is, for example, a prismatic, cylindrical, conical, or hemispherical shape, or a combination thereof. With respect to the size of each tank, for example, if the tank is a cylinder, it has preferably a diameter in the range of 1 to 20 mm and a depth in the range of 2 to 20 mm. The shapes and sizes of the respective tanks all may be identical to one another or may be different from one another. In this example, the number of the plurality of tanks is 10, but the present invention is not limited thereto. The number of the plurality of tanks can be determined suitably with consideration given to, for example, the number of reagents to be used and operability.

As described above, it is preferable that the plurality of tanks 110 to 119 include a storage tank, a reaction tank, and a preparation tank.

The storage tank is used for storing a reagent. The storage tank may be only one of the plurality of tanks 110 to 119 or two or more of them.

The reaction tank is used for reacting the reagent and a sample. The reaction tank also may be only one of the plurality of tanks 110 to 119 or two or more of them.

The preparation tank is used for preparing the sample. The preparation tank also may be only one of the plurality of tanks 110 to 119 or two or more of them.

Preferably, the plurality of tanks 110 to 119 further include a sample tank.

The sample tank is used in directly injecting a sample into the cartridge 100. The sample tank also may be only one of the plurality of tanks 110 to 119 or two or more of them.

The waste liquid tanks 120 to 122 are used for removing a residual liquid from the pipette. Each of the waste liquid tanks 120 to 122 has a capillary phenomenon generation portion. The residual liquid present at the leading end of the pipette is brought into contact with a capillary phenomenon generation portion of the waste liquid tanks 120 to 122, so that the residual liquid is transferred to the capillary phenomenon generation portion.

The shape of each tank of the waste liquid tanks 120 to 122 is not particularly limited and is, for example, prismatic or cylindrical. The size of each tank of the waste liquid tanks 120 to 122 is not particularly limited and can be determined suitably with consideration given to, for example, the size (diameter) and shape of the leading end of the pipette. For example, if the tank is a prismatic column, each of the width and length thereof is, for example, in the range of 3 to 5 mm, and the depth thereof is, for example, in the range of 0.5 to 10 mm and preferably in the range of 1 to 3 mm. The shapes and sizes of the respective tanks of the waste liquid tanks 120 to 122 all may be identical to one another or may be different from one another. In this example, the number of the waste liquid tanks is three, but the present invention is not limited thereto. The number of the waste liquid tanks is as described above.

As described above, preferably, the capillary phenomenon generation portion is a space that is formed in at least one of the bottom and side walls of each of the waste liquid tanks 120 to 122 and that allows a capillary phenomenon to be generated. Examples of the method of forming a space that allows a capillary phenomenon to be generated, in at least one of the bottom and side walls of each of the waste liquid tanks 120 to 122, include a method of forming a groove and a method of forming mesh-like concavities and convexities, in at least one of the bottom and side walls of each of the waste liquid tanks 120 to 122. These methods can simplify the process for producing the cartridge. Particularly, the method of forming a groove in at least one of the bottom and side walls of each of the waste liquid tanks 120 to 122 is preferable since it allows the residual liquid to be removed more efficiently.

Next, the waste liquid tank of the present invention is described using an example in which a space for generating a capillary phenomenon is formed in the bottom.

Figure 3:
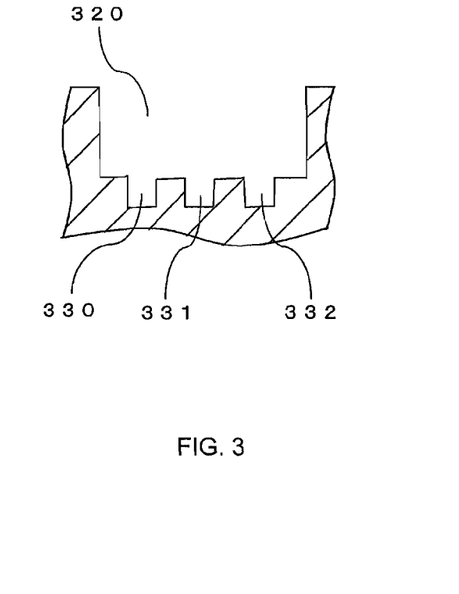
FIG. 3 is a cross-sectional view of an example of the waste liquid tank according to the present invention with grooves formed in the bottom thereof.

FIG. 3 shows a cross-sectional view of an example of the waste liquid tank according to the present invention with grooves formed in the bottom thereof. As shown in FIG. 3, three grooves 330 to 332 are formed in the bottom of the waste liquid tank 320.

The width of the grooves is not particularly limited and can be determined suitably with consideration given to, for example, the size (diameter) of the leading end of the pipette and the size of a droplet formed at the leading end of the pipette. The width is, for example, in the range of 0.1 to 1 mm and preferably in the range of 0.3 to 0.6 mm. The depth of the grooves is not particularly limited and can be determined suitably with consideration given to, for example, the ease of removing the cartridge from a mold when molding it, i.e. moldability. The depth is, for example, in the range of 0.3 to 1 mm, preferably in the range of 0.4 to 0.7 mm, and more preferably 0.6 mm. The length of the grooves is identical to the width or length of the waste liquid tanks. The number of the grooves can be determined suitably according to the size of the waste liquid tanks.

Figure 4:
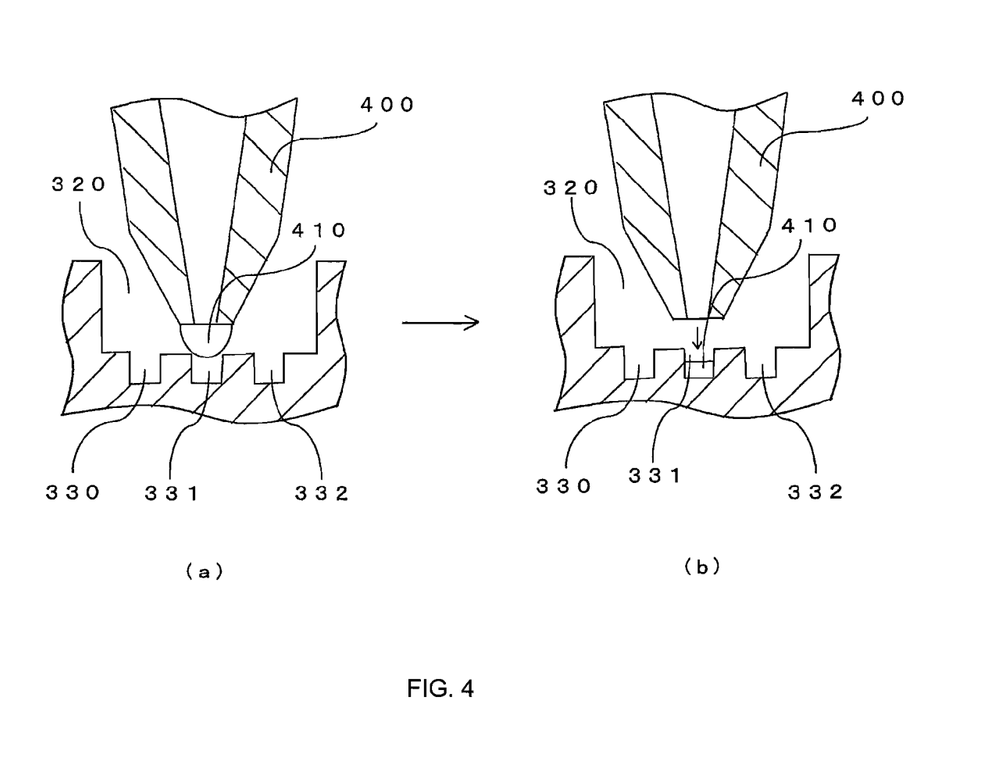
FIG. 4 shows cross-sectional views for explaining the state of transferring a residual liquid present at the leading end of a pipette to a space at the bottom of the waste liquid tank, in an example of the waste liquid tank according to the present invention.

FIG. 4 shows the state of transferring the residual liquid to the space. In FIG. 4, identical parts to those shown in FIG. 3 are indicated with the same numerals. As shown in FIG. 4(a), when the residual liquid 410 is to be transferred to the space, the residual liquid 410 present at the leading end of the pipette 400 is brought into contact with the space (the groove 331 in this example) first. Then, as shown with an arrow in FIG. 4(b), the residual liquid 410 is transferred to the space through the capillary phenomenon. At this time, the distance between the space and the leading end of the pipette 400 is not particularly limited as long as the distance allows the residual liquid 410 to be brought into contact with the space. The distance is, for example, in the range of 0.0 to 0.7 mm and preferably 0.5 mm.

The capillary phenomenon generation portion may be a porous body disposed in each of the waste liquid tanks 120 to 122. The place where the porous body is disposed is not particularly limited and can be, for example, the bottom or side walls of each waste liquid tank. Examples of the method of disposing a porous body in at least one of the bottom and side walls of each of the waste liquid tanks 120 to 122 include a method of fixing the porous body to at least one of the bottom and side walls of each of the waste liquid tanks 120 to 122, using, for example, an adhesive. When being disposed on the bottom of each of the waste liquid tanks 120 to 122, the porous body may merely be placed on the bottom of each of the waste liquid tanks 120 to 122 without using, for example, an adhesive.

Figure 5:
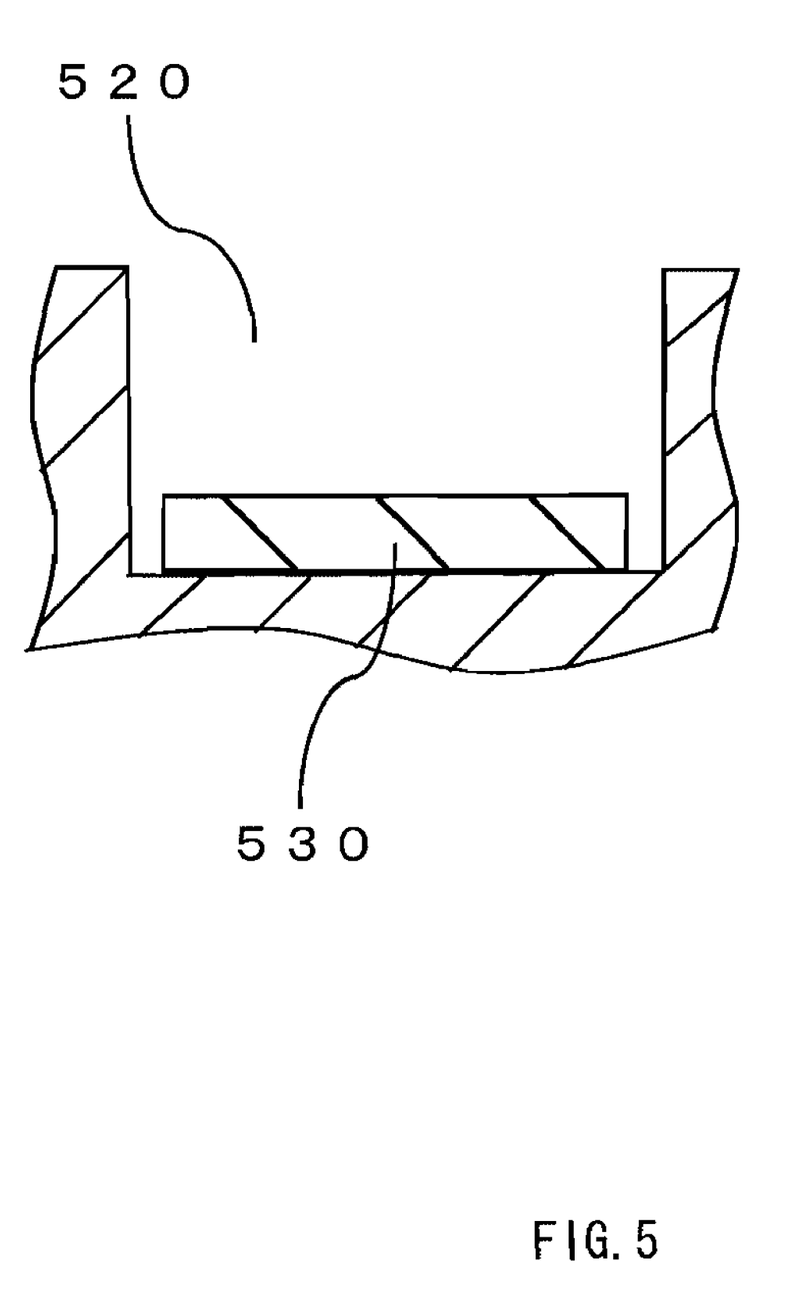
FIG. 5 is a cross-sectional view of an example of the waste liquid tank according to the present invention with a porous body disposed on the bottom thereof.

FIG. 5 shows a cross-sectional view of an example of a waste liquid tank according to the present invention with a porous body placed on the bottom. As shown in FIG. 5, a porous body 530 is disposed on the bottom of the waste liquid tank 520.

Examples of the porous body include filter paper, non-woven fabric, knitting, fabric, open-cell foamed resin, and sponge. The size of the porous body can be determined suitably according to, for example, the area of the bottom of the waste liquid tank.

Preferably, the porous body is replaced with every measurement. However, it also is possible to use the cartridge for a plurality of measurements without replacing the porous body.

As described above, in the cartridge 100 shown in FIGS. 1 and 2, the waste liquid tanks 120 to 122 are disposed at one end thereof (the left end in FIGS. 1 and 2). However, the cartridge of the present invention is not limited thereto. In the cartridge of the present invention, the waste liquid tanks may be disposed in any position in the cartridge. For instance, they may be disposed in the middle in the longitudinal direction of the cartridge so as to be placed in the middle of the plurality of tanks, or they may be disposed at an end in the width direction of the cartridge so as to be in parallel with the plurality of tanks.

As described above, in the cartridge of the present invention, in order to prevent any foreign substance from being mixed, it is preferable that before use, a part or all of the upper openings of the plurality of tanks be sealed with a sealing material. Examples of the sealing material include metallic foil such as aluminum foil and a polymer film. Preferably, the sealing material is aluminum foil, as the pipette can break it easily and it has good sealing performance. A part or all of the upper openings of the plurality of tanks can be sealed by allowing the sealing material to adhere to the upper surface of the cartridge with, for example, a hot-melt adhesive.

Figure 6:
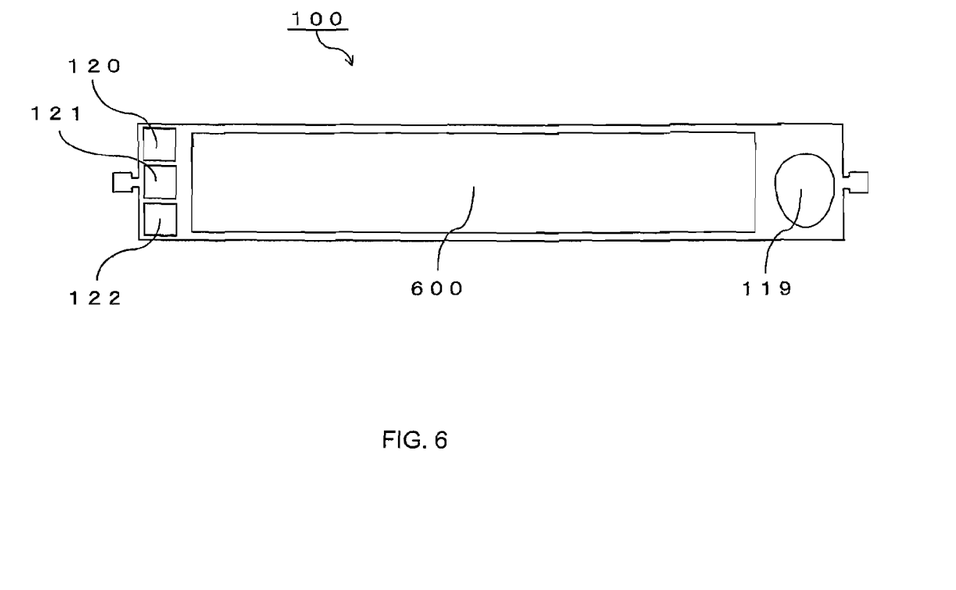
FIG. 6 is a plan view showing the configuration of an example of the cartridge according to the present invention, with a part of the upper openings of a plurality of tanks being sealed.

FIG. 6 shows the configuration of an example of the cartridge according to the present invention, with a part of the upper openings of the plurality of tanks being sealed. The cartridge shown in FIG. 6 has the same configuration as that shown in FIGS. 1 and 2 except for having the sealing material. Identical parts as those shown in FIGS. 1 and 2 are indicated with the same numerals. As shown in FIG. 6, in this cartridge 100, the upper openings of the tanks 110 to 118 out of the plurality of tanks 110 to 119 are sealed with a sealing material 600 (see FIGS. 1 and 2).

The method of producing the cartridge of the present invention is not particularly limited. The cartridge of the present invention in which the capillary phenomenon generation portion of each waste liquid tank is the aforementioned space can be produced by, for example, integral molding such as injection molding. Furthermore, the cartridge of the present invention in which the capillary phenomenon generation portion of each waste liquid tank is the aforementioned porous body can be produced by molding a cartridge body by, for example, injection molding and then placing the porous body in the waste liquid tank. The cartridge of the present invention can be produced in large quantities with uniform quality by producing a molded body including a plurality of cartridges of the present invention that are joined together, by, for example, injection molding, sealing a part or all of the upper openings of the plurality of tanks in each cartridge of the molded body, and processing the molded body suitably as required so that the molded body can be separated into individual cartridges, each of which has been sealed. Examples of the process for separating the molded body into individual cartridges include processes such as formation of perforations, formation of a recessed line, and formation of a notch.

When the cartridge 100 shown in FIGS. 1 and 2 is used, for example, for measuring a predetermined component in a sample blood through latex agglutination, the tanks 112 to 116 are used as first to fifth storage tanks, the tanks 111, 117, and 118 as first to third reaction tanks, the tank 110 as the preparation tank, and the tank 119 as the sample tank.

In the first storage tank 112, for example, a hemoglobin measurement reagent is stored. The hemoglobin measurement reagent is used for measuring the hemoglobin concentration in a red blood cell. Known various reagents can be used as long as they react with hemoglobin and can colorimetrically determine the state after the reaction. The hemoglobin concentration is measured to calculate the hematocrit value (the volume ratio of red blood cells in blood) from the hemoglobin concentration and to compensate the effect of the hematocrit value in the measurement.

In the second storage tank 113, for example, a diluent for hemolysis is stored. The diluent for hemolysis is used for destroying a blood corpuscle component in order to measure the component in the blood corpuscle. For example, a diluent containing saponin in physiological saline is used.

A buffer solution to be used as, for example, a diluent and a cleaning liquid is stored in the third storage tank 114. Preferably, the buffer solution is one that does not inhibit the reaction of hemoglobin and immunoreactions of a component to be measured and that does not cause an error in the absorbance measurement of hemoglobin and a component to be measured. For example, physiological saline or bovine serum albumin can be used.

In the fourth storage tank 115, for example, a cleaning liquid is stored. The cleaning liquid is used for washing a pipette provided for the automatic analyzer described later and, for example, distilled water is used. The cleaning liquid to be used also can be one other than distilled water.

In the fifth storage tank 116, for example, a latex suspension is stored. Generally, the latex suspension is one in which an immunoreactive material that exhibits specific reactivity to a component to be measured is dispersed in a buffer solution, with the immunoreactive material being supported by latex microparticles. Examples of the component to be measured include disease markers such as hepatitis virus, rheumatoid factor, C-reactive protein, hemolytic streptococcal toxins, and various enzymes. The immunoreactive material to be used herein can be, for example, one that exhibits an antigen-antibody reaction specifically with one of the disease markers described as examples and thereby generates an aggregate. Examples of the latex microparticles include polystyrene latex beads.

The first reaction tank 111 is used in, for example, preparing a mixture of diluted blood and a hemoglobin measurement reagent and measuring the absorbance of the mixture. In other words, the first reaction tank is used, for example, for obtaining the absorbance required for calculating the hemoglobin concentration.

The second reaction tank 117 is used in, for example, generating a latex agglutination reaction and measuring the absorbance at that time.

The third reaction tank 118 is used for measuring the absorbance by generating a different immunoreactions from that generated in the second reaction tank in order to measure a different component to be measured from that in the second reaction tank or for measuring the absorbance by generating a similar immunoreaction to that generated in the second reaction tank in order to check the measurement reproducibility.

The preparation tank 110 is used, for example, for preparing the sample blood. The sample blood is prepared by, for example, mixing the sample blood with the physiological saline stored in the third storage tank to dilute the blood.

For example, the sample blood is injected into the sample tank 119.

With this case used as an example, the measurement using a cartridge of the present invention is described. In this measurement, the residual liquid removing method of the present invention is carried out. The cartridge of the present invention used in this example has waste liquid tanks with the configuration shown in FIG. 3.

Figure 7:
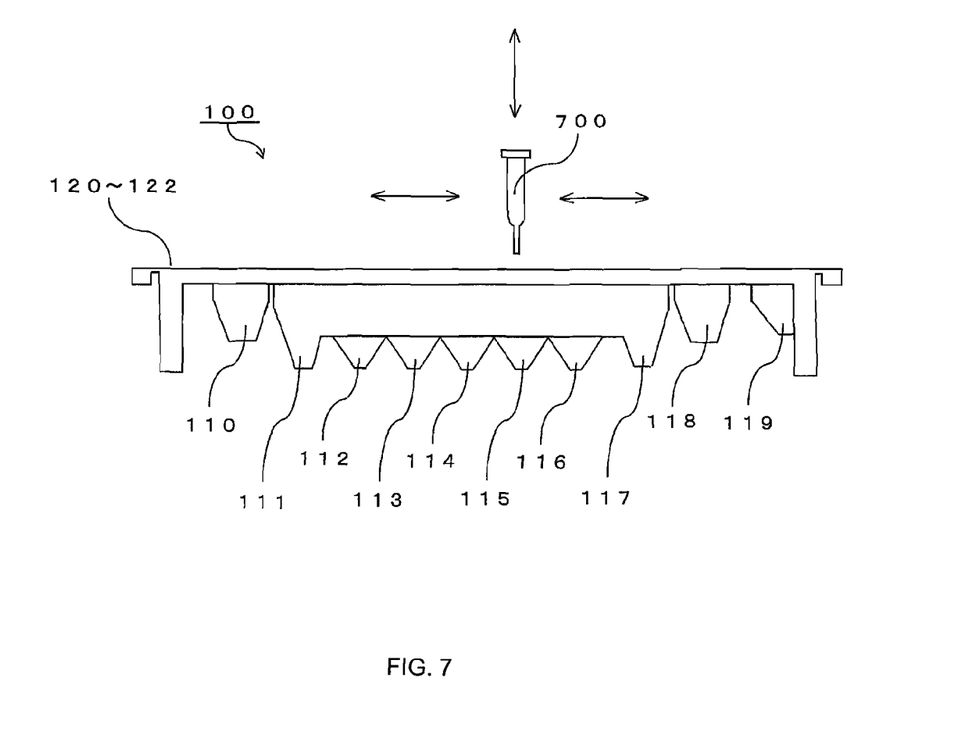
FIG. 7 is a diagram for explaining the state of introducing or leading out a sample or a reagent stored in a plurality of tanks with a pipette, in an example of the cartridge of the present invention.

For example, the cartridge 100 of the present invention is used for an automatic analyzer of the present invention, into which it is incorporated. One cartridge may be incorporated into the automatic analyzer or a plurality of cartridges may be incorporated into the automatic analyzer at the same time. The automatic analyzer is equipped with a pipette. The pipette is movable vertically and horizontally. The pipette introduces or leads out, for example, a sample or a reagent stored in a plurality of tanks 110 to 119 of the cartridge 100. FIG. 7 shows the state where the pipette introduces or leads out, for example, a sample or a reagent stored in a plurality of tanks of the cartridge. In FIG. 7, identical parts to those shown in FIGS. 1 and 2 are indicated with the same numerals. As shown in FIG. 7, in this cartridge 100, for example, introduction or leading out of the sample or reagent stored in the plurality of tanks 110 to 119 is carried out with a vertically and horizontally movable pipette 700. Hereinafter, the action of introducing a liquid from a tank and leading out the liquid to another tank is referred to as "dispense".

First, after sample blood is held in the sample tank 119, the cartridge 100 is mounted on an automatic analyzer.

In the automatic analyzer, it is recognized automatically or according to the user's operation that the cartridge 100 has been mounted, and then the measurement operation starts. This measurement operation includes measurements of a hemoglobin concentration and a component to be measured.

Next, the hemoglobin concentration is measured. The measurement of the hemoglobin concentration includes, for example, sample preparation, absorbance measurement, and calculation of the hemoglobin concentration (hematocrit value).

In the sample preparation, first, physiological saline stored in the second storage tank 113 is dispensed with the pipette 700 with respect to the preparation tank 110. With respect to the preparation tank 110, for example, 95 µL of physiological saline is dispensed twice and thereby a total of 190 µL, of physiological saline is dispensed.

Next, the buffer solution stored in the third storage tank 114 is dispensed with the pipette 700 with respect to the second reaction tank 117. With respect to the second reaction tank 117, for example, 84 µL of buffer solution is dispensed at one time. Subsequently, the hemoglobin measurement reagent stored in the first storage tank 112 is dispensed with the pipette 700 with respect to the first reaction tank 111. With respect to the first reaction tank 111, for example, 77 µL of hemoglobin measurement reagent is dispensed twice and thereby a total of 154 µL of hemoglobin measurement reagent is dispensed.

Next, the pipette 700 is washed. Specifically, the leading end of the pipette 700 is moved to the second storage tank 113 first, and introduction and leading out of 110 µL of physiological saline stored in the second storage tank 113 are repeated twice. Subsequently, the leading end of the pipette 700 is moved to the fourth storage tank 115, and 50 µL of distilled water stored in the fourth storage tank 115 is introduced thereinto and led out therefrom. Thereafter, the pipette 700 is moved to the waste liquid tank 120, and the leading end of the pipette 700 is brought into contact with the groove of the bottom of the waste liquid tank 120. As a result, the residual liquid present at the leading end of the pipette 700 (for example, a droplet present outside the leading end of a pipette due to its own weight) is absorbed into the groove of the bottom of the waste liquid tank 120 through the capillary phenomenon.

Next, the sample blood held in the sample tank 119 is dispensed with the pipette 700 with respect to the preparation tank 110 and the liquid inside the preparation tank 110 is then mixed, so that the sample blood is diluted. With respect to the preparation tank 110, for example, 28 µL of the sample blood is dispensed at one time, and the liquid inside the preparation tank 110 is mixed by, for example, repeating introduction and leading out of 110 µL of the liquid five times.

Subsequently, the pipette 700 is washed again through the same procedure as that used in washing of the pipette, which is described above.

Finally, after the diluted blood in the preparation tank 110 is dispensed with the pipette 700 with respect to the first reaction tank 111, the liquid inside the first reaction tank 111 is mixed. Thus, the preparation of the sample for measuring hemoglobin is completed. With respect to the first reaction tank 111, for example, 28 µL of diluted blood is dispensed at one time, and the liquid inside the first reaction tank 111 is mixed by, for example, repeating introduction and leading out of 110 µL of the liquid five times.

Next, the absorbance measurement is carried out. The absorbance is measured by irradiating the first reaction tank 111 with monochromatic light from a side thereof and measuring the amount of light transmitted through the first reaction tank 111 at that time. The monochromatic light is selected according to the type of the reagent for measuring hemoglobin. It can be, for example, one with a wavelength of 540 nm. The hemoglobin concentration is calculated by, for example, substituting the difference between a reference absorbance and a measured absorbance for an arithmetic expression. From the hemoglobin concentration thus obtained, a hematocrit value can be calculated. However, the hematocrit value also may be calculated directly based on the measured absorbance without measuring the hemoglobin concentration.

After completion of measurement of the hemoglobin concentration (hematocrit value), as described above, the concentration of a component to be measured is determined. The determination of the concentration of the component to be measured include, for example, sample preparation, absorbance measurement, and concentration calculation.

To prepare the sample, the pipette 700 is washed first. Specifically, first, the leading end of the pipette 700 is moved to the second storage tank 113, and introduction and leading out of 110 µL, of physiological saline stored in the second storage tank 113 are repeated twice. Subsequently, the leading end of the pipette 700 is moved to the fourth storage tank 115, and 50 µL of distilled water stored in the fourth storage tank 115 is introduced thereinto and led out therefrom. Thereafter, the pipette 700 is moved to the waste liquid tank 120, and the leading end of the pipette 700 is brought into contact with the groove of the bottom of the waste liquid tank 120. As a result, the residual liquid present at the leading end of the pipette 700 is absorbed into the groove of the bottom of the waste liquid tank 120 through the capillary phenomenon.

Next, the diluted blood inside the preparation tank 110 is dispensed with the pipette 700 with respect to the second reaction tank 117 and the liquid inside the second reaction tank 117 is mixed. With respect to the second reaction tank 117, for example, 28 µL of diluted blood is dispensed at one time. The liquid inside the second reaction tank 117 is mixed by, for example, repeating introduction and leading out of 85 µL of the liquid five times.

Next, using the distilled water stored in the fourth storage tank 115, the pipette 700 is washed. Specifically, first, the leading end of the pipette 700 is moved to the fourth storage tank 115, and introduction and leading out of 110 µL of distilled water stored in the fourth storage tank 115 are repeated three times. Subsequently, the pipette 700 is moved to the waste liquid tank 120 and the leading end of the pipette 700 is brought into contact with the groove of the bottom of the waste liquid tank 120. As a result, the residual liquid present at the leading end of the pipette 700 is absorbed into the groove of the bottom of the waste liquid tank 120 through the capillary phenomenon.

Finally, the latex suspension stored in the fifth storage tank 116 is dispensed with the pipette 700 with respect to the second reaction tank 117 and the liquid inside the second reaction tank 117 is mixed. With respect to the second reaction tank 117, for example, 28.2 µL of latex suspension is dispensed at one time. The liquid inside the second reaction tank 117 is mixed by, for example, repeating introduction and leading out of 110 µL of the liquid three times.

Next, the absorbance measurement is carried out. The absorbance is measured by irradiating the second reaction tank 117 with monochromatic light from a side thereof and measuring the amount of light transmitted through the second reaction tank 117 at that time. The monochromatic light is selected according to the component to be measured and the immunoreactive material supported by the latex suspension to be used. The concentration of the component to be measured is calculated by, for example, substituting the difference between a reference absorbance and a measured absorbance for an arithmetic expression. The concentration of the component to be measured thus obtained is compensated based on the hematocrit value obtained beforehand.

Thus, one measurement is completed. Then the pipette 700 is moved to the waste liquid tank 121 and the leading end of the pipette 700 is brought into contact with the groove of the bottom of the waste liquid tank 121. As a result, the residual liquid present at the leading end of the pipette 700 is absorbed into the groove of the bottom of the waste liquid tank 121 through the capillary phenomenon. Accordingly, the pipette 700 can be used for the next measurement without being discarded.

As described above, in the measurement using a cartridge of the present invention including a plurality of waste liquid tanks, it is possible to transfer the cleaning liquid used during the first measurement and the residual liquid present at the leading end of the pipette before the second measurement into the grooves of the bottoms of separate waste liquid tanks. This makes it possible to prevent different types of residual liquids from being contaminated with one another.

The cartridge of the present invention can be used for measurement by not only the aforementioned latex agglutination but also, for example, immunonephelometry, an enzymatic colorimetric method, and immunonephelometric agglutination inhibition assay. Examples of the component to be measured by the immunonephelometry include microalbumin. Examples of the component to be measured by the enzymatic colorimetric method include creatine. Examples of the component to be measured by the immunonephelometric agglutination inhibition assay include hemoglobin A1c.

INDUSTRIAL APPLICABILITY

The cartridge of the present invention can remove a residual liquid all around the leading end of a pipette, without requiring any new equipment, regardless of the viscosity of the residual liquid. The cartridge of the present invention is incorporated into, for example, an automatic analyzer to be used suitably for measurement using immunoassays including latex agglutination. The intended use thereof is not limited and it is applicable over a wide range of fields.

The invention claimed is:

1. A cartridge comprising a plurality of tanks, each of which has an upper opening, a liquid being introduced into or led out from at least one of the plurality of tanks with a pipette,
    wherein the cartridge further comprises a waste liquid tank,
    a plurality of spaces are formed in at least one of a bottom and side walls of the waste liquid tank, each of the spaces allowing a capillary phenomenon to be generated,
    each of the spaces is configured so that when a residual liquid present at a leading end of a pipette is brought into contact with one of the spaces, the residual liquid is removed from the pipette and transferred to the one of the spaces through the capillary phenomenon,
    each of the spaces is a groove, and
    each of the grooves has a width in a range of 0.1 to 1 mm and a depth in a range of 0.3 to 1 mm.

2. The cartridge according to claim 1, wherein the cartridge comprises a plurality of the waste liquid tanks.

3. The cartridge according to claim 2, wherein the number of the waste liquid tanks is in a range of 2 to 6.

4. The cartridge according to claim 1, wherein when the residual liquid is transferred to the one of the spaces that allows the capillary phenomenon to be generated, the distance between the leading end of the pipette and the one of the spaces is in a range of 0.0 to 0.7 mm.

5. The cartridge according to claim 1, wherein the plurality of tanks comprise a storage tank for storing a reagent and a reaction tank for reacting the reagent and a sample.

6. The cartridge according to claim 5, wherein the plurality of tanks further comprise a preparation tank for preparing the sample.

7. The cartridge according to claim 1, wherein at least one of the plurality of tanks is used as a measurement cell for measuring absorbance.

8. The cartridge according to claim 1, wherein the whole cartridge has a length in a range of 1 to 10 cm, a width in a range of 0.3 to 3 cm, and a height in a range of 0.5 to 5 cm.

9. The cartridge according to claim 1, wherein before use, a part or all of the upper openings of the plurality of tanks is sealed with a sealing material.

10. The cartridge according to claim 9, wherein the sealing material is aluminum foil.

11. The cartridge according to claim 1, wherein the cartridge is configured for use in an automatic analyzer for analyzing a sample.

* * * * *